| United States Patent [19] | [11] | 4,236,905 |
|---|---|---|
| Dabby et al. | [45] | Dec. 2, 1980 |

[54] METHOD FOR CONTINUOUSLY MONITORING THE COMPOSITION OF GLASS PARTICULATE DURING THE PRODUCTION OF OPTICAL FIBER

[75] Inventors: Franklin W. Dabby, Woodbridge; Ronald B. Chesler, Cheshire, both of Conn.

[73] Assignee: Times Fiber Communications, Inc., Wallingford, Conn.

[21] Appl. No.: 57,457

[22] Filed: Jul. 13, 1979

[51] Int. Cl.$^3$ ............... C03B 20/00; C03B 37/07; C03B 37/075
[52] U.S. Cl. .......................... 65/3 A; 65/18; 65/29
[58] Field of Search ............... 65/3 A, 18, 29

[56] References Cited

U.S. PATENT DOCUMENTS 3,932,160  1/1976  Camlibel et al. .............. 65/3 A

OTHER PUBLICATIONS

Wood et al., "Investigations ... By Infra-red Spectroscopy" Journal of Materials Science 13 (1978) pp. 1761–1768.

*Primary Examiner*—Richard V. Fisher
*Attorney, Agent, or Firm*—Bacon & Thomas

[57] ABSTRACT

A process for continuously monitoring the content of boron oxide in a stream of borosilicate particles as it is applied to a glass rod during the production of optical fiber is disclosed. Monitoring is accomplished by continuously measuring the infra-red absorption bands of the particles at or near the point of deposition on the rod.

6 Claims, No Drawings

METHOD FOR CONTINUOUSLY MONITORING THE COMPOSITION OF GLASS PARTICULATE DURING THE PRODUCTION OF OPTICAL FIBER

BACKGROUND OF THE INVENTION

1. Field of the Invention

The present invention is directed to an improved process for the manufacture of optical fiber.

2. Description of the Prior Art

During the past decade, a great deal of work has been undertaken directed to the manufacture of glass transmission lines for visible and near-visible electromagnetic radiation, commonly referred to as optical waveguides or optical fiber. In brief, optical waveguides are extremely thin, flexible glass fibers, prepared by drawing glass preforms under controlled conditions. Although these conditions are subject to wide variation, depending upon such factors as the composition of the glass and the drawing procedure, the optical waveguide so prepared will comprise, in its simplest form, a glass core of a given constant diameter, surrounded by a glass cladding having an index of refraction less than that of the glass core. The cladding acts as a barrier which confines the light to the core.

While the drawing procedure is important in obtaining a properly functioning optical waveguide, it is the production of the glass preform which is drawn into the fiber which controls the ultimate composition and hence transmission properties of the waveguide. Thus far, workers in the art have proposed to manufacture such preforms in several ways. One method, described in U.S. Pat. No. 3,932,160, forms a glass preform by deposition of borosilicate particulate on a pure silica start rod by high temperature pyrolysis of a gaseous mixture of silane and borane or a gaseous mixture of silicon tetrachloride and boron trichloride. The temperatures required to effect the pyrolysis reaction can be produced by conducting the deposition in a reaction furnace which heats both the gaseous mixture of reactants and the glass rod. Alternately, the requisite temperatures can be obtained by directing the reactants through a natural gas flame in the presence of oxygen. The pyrolysis reaction produces fine particles of borosilicate glass which are deposited on the pure fused silica start rod and, upon sintering, form the outer region of the core and cladding of the preform.

To produce a preform having a graded profile, that is, a radially varying index of refraction, the ratio of the silicon containing reactant to the boron containing reactant in the gaseous mixture is varied in such a manner that borosilicate particulate having increasing proportions of boron oxide relative to silica is produced. Moreover, to insure that the deposition of borosilicate is uniform for a given radial distance from the preform core, the start rod must be simultaneously translated and rotated to provide even distribution of the particulate over the length of the rod. Thus, by setting a uniform translation and rotation rate for the start rod, the concentration of components in the gaseous reactant mixture can be continuously varied so as to achieve the desired radial concentration profile of borosilicate which is uniform for any given radial distance from the silica core.

However, as the nature of optical waveguides is such that slight descrepancies in composition may cause significant deleterious results in transmission capability, it is desirable to provide means for precisely controlling the deposition of the borosilicate particulate on the start rod to insure production of a preform having the desired radial composition profile.

SUMMARY OF THE INVENTION

Accordingly, it is an object of the present invention to provide a method for preparing a preform which can be drawn into optical fiber, which allows for the precise control of the composition of the borosilicate deposited on the glass start rod.

Another object of the invention is to provide a means of continuously monitoring the composition of the borosilicate particulate so as to insure the obtainment of a borosilicate clad preform having a uniform, graded index of refraction.

Still other objects and advantages of the invention will become apparent to those of skill in the art upon review of the entire disclosure herein.

The foregoing objects and advantages are accomplished by providing a process for the production of optical fiber which comprises preparing a preform by depositing and sintering borosilicate particles on a cylindrical glass rod, heating the preform to the drawing temperature and drawing it into optical fiber, in which the composition of the borosilicate particulate being deposited on the rod is continuously monitored via infra-red spectrophotometry.

DETAILED DESCRIPTION OF THE INVENTION

The borosilicate particles can be produced by high temperature pyrolysis of a first gaseous reactant selected from $SiH_4$, $SiCl_4$ and $SiBr_4$ and a second gaseous reactant selected from $B_2H_6$, $BCl_3$ and $BBr_3$.

In conventional methods for preparing glass preforms by depositing and sintering borosilicate particles on a glass start rod, the composition of the borosilicate particulate is controlled by adjusting the flow of the reactant gases, particularly the boron containing reactant, generally boron trichloride, which is subjected to high temperature pyrolysis. Typically, the flow of boron trichloride is adjusted in response to the weight of the particulate deposited or the time from the beginning of the deposition on the start rod. As time and weight increase, the flow of boron trichloride to the pyrolysis reaction is increased which, in turn, increases the concentration of boron oxide in the borosilicate particulate produced by the reaction. When a final, pre-determined time or weight is reached, the flow of reactant gases if shut off and the rod is heated to the sintering temperature to produce the preform.

A significant drawback to the time and/or weight determinative methods is that they presume ideal stoichiometric conditions for the pyrolysis reaction. However, as such ideal conditions are not necessarily achieved, it is desirable to provide additional monitoring means for insuring that particles of the desired composition are deposited. The use of infra-red absorption spectrophotometric analysis of the particulate stream provides this capability. A discussion of the infra-red absorption characteristics of high temperature reactions of silicon tetrachloride and oxygen is provided by Wood et al, "Investigation of the Reactions of $SiCl_4$ and $O_2$ at Elevated Temperatures by Infra-red Spectroscopy", Journal of Materials Science 13 (1978) pp. 1761–1768, the disclosure of which is hereby incorporated by reference.

By continuous examination of the infra-red absorption bands exhibited by the particulate stream leaving the pyrolysis reaction zone, the composition of the stream in terms of the ratio of boron oxide to silica can be determined. This serves as a check of the stoichiometric precision of the pyrolysis reaction and insures that particulate of the appropriate composition is deposited. A device known to those of skill in the art as a monochromator provides the means for continuously monitoring the infra-red absorption bands of the particulate as it proceeds from the pyrolysis reaction zone to the glass rod.

The monochromator is preferably electronically connected to the valves which regulate the flow of boron trichloride gas to the pyrolysis reaction. Hence, if the infra-red absorption band indicates that the particulate stream is deficient in a constituent such as boron oxide relative to silica, the valve will be automatically adjusted to increase the flow of boron trichloride to the reaction zone, and vice versa. The silica content of the particulate stream is monitored in the same manner as the boron oxide, but at a different infra-red wavelength.

The process of the present invention thus, allows for the continuous and automatic control of the composition of the particulate deposited on the glass start rod. In this manner, a borosilicate deposit may be built up along the length of the rod which, upon sintering, exhibits a radially varying index of refraction as desired. Accordingly, highly precise optical fiber preforms can be prepared.

Drawing of the glass preform is accomplished in a separate drawing furnace where the preform is heated to the drawing temperature and drawn into fiber. The specifics of such drawing operations are well known to those of skill in the art.

While the present invention has now been described in terms of certain preferred embodiments, the skilled artisan will readily appreciate that various modifications, changes, substitutions and omissions may be made without departing from the spirit thereof. It is intended, therefore, that the present invention be limited solely by the scope of the following claims.

What is claimed is:

1. In a process for the production of optical fiber which comprises preparing a preform by depositing and sintering borosilicate particles on a cylindrical glass rod, heating said preform to the drawing temperature and drawing said preform into optical fiber, the improvement comprising continuously monitoring the boron oxide content of the borosilicate particles as they are deposited via infra-red spectrophotometry.

2. The process as defined by claim 1, wherein said borosilicate particles are produced by high temperature pyrolysis of a first gaseous reactant selected from the group consisting of $SiH_4$, $SiCl_4$ and $SiBr_4$ and a second gaseous reactant selected from the group consisting of $B_2H_6$, $BCl_3$ and $BBr_3$.

3. The process as defined by claim 2, wherein said reactants are $SiCl_4$ and $BCl_3$.

4. The process as defined by claim 3, wherein the composition of the borosilicate particles is adjusted by changing the flow of $BCl_3$ reactant admitted to the pyrolysis reaction.

5. The process as defined by claim 4, wherein said continuous monitoring of the boron oxide content of the borosilicate particles is achieved by a monochromator disposed between said pyrolysis reaction and said cylindrical glass rod.

6. The process as defined by claim 5, wherein said flow of $BCl_3$ reactant admitted to the pyrolysis reaction is changed in response to readings of said monochromator.

* * * * *